United States Patent
Ou (10) Patent No.: US 10,548,831 B2
(45) Date of Patent: Feb. 4, 2020

(54) ANHYDROUS COMPOSITION OF SMALL-MOLECULE POLYSACCHARIDES AND APPLICATION THEREOF

(71) Applicant: SAGE PHARMACEUTICALS, INC., Alhambra, CA (US)

(72) Inventor: Tsung-Yu Ou, Alhambra, CA (US)

(73) Assignee: SAGE PHARMACEUTICALS, INC., Alhambra, CA (US)

( * ) Notice: Subject to any disclaimer, the term of this patent is extended or adjusted under 35 U.S.C. 154(b) by 214 days.

(21) Appl. No.: 15/149,758

(22) Filed: May 9, 2016

(65) Prior Publication Data
US 2017/0252282 A1 Sep. 7, 2017

(30) Foreign Application Priority Data
Mar. 2, 2016 (TW) .............................. 105106381 A (51) Int. Cl.
| | |
|---|---|
| *A61K 8/73* | (2006.01) |
| *A61K 8/34* | (2006.01) |
| *A61Q 19/00* | (2006.01) |
| *A61Q 19/08* | (2006.01) |

(52) U.S. Cl.
CPC .............. *A61K 8/735* (2013.01); *A61K 8/345* (2013.01); *A61Q 19/007* (2013.01); *A61Q 19/08* (2013.01); *A61K 2800/31* (2013.01)

(58) Field of Classification Search
None
See application file for complete search history.

(56) References Cited

U.S. PATENT DOCUMENTS

| | | | |
|---|---|---|---|
| 2007/0196312 A1* | 8/2007 | Gross ................... | A61K 8/0212 424/70.13 |
| 2008/0206159 A1* | 8/2008 | Tamarkin ............... | A61K 9/122 424/45 |
| 2015/0175991 A1* | 6/2015 | Guo ......................... | C12R 1/07 424/59 |

OTHER PUBLICATIONS

Bloomage. "Trend of HA in Personal Care Industry" <http://www.in-cosmetics.com/RXUK/RXUK_InCosmetics/2015-Website/Documents/in-cos15,IS,T3,D1,Hymagic%20A%20new%20solution%20for%20dry%20skin,Haiying%20Wang.pdf?v=635653962085574911> Available May 2, 2015; accessed Sep. 27, 2017 (Year: 2015).*
MiniHA. Bloomage. <http://www.bloomagefreda.com/appen/id/7.html.> Available Aug. 8, 2015; accessed Sep. 2017 (Year: 2015).*

* cited by examiner

*Primary Examiner* — Nicole P Babson
(74) *Attorney, Agent, or Firm* — Muncy, Geissler, Olds & Lowe, P.C.

(57) ABSTRACT

The present invention provides a novel anhydrous composition of small-molecule polysaccharides, consisting of at least a small-molecule polysaccharide and an anhydrous base. The formulation of the anhydrous composition of small-molecule polysaccharides allows the small-molecule polysaccharide to maintain a molecular size of 12-22 nm and the direct penetration of the small-molecule polysaccharide across the horny layer of skin. The present invention also provides a method of effectively maintaining skin hydration level in a subject in need thereof, comprising topically administering to the subject an anhydrous composition of small-molecule polysaccharides.

4 Claims, 10 Drawing Sheets

ANHYDROUS COMPOSITION OF SMALL-MOLECULE POLYSACCHARIDES AND APPLICATION THEREOF

CROSS-REFERENCE TO RELATED APPLICATION

This application claims priority of Taiwan patent application No. 105106381, filed on Mar. 2, 2016, the content of which is incorporated herein in its entirety by reference.

BACKGROUND OF THE INVENTION

1. Field of the Invention

The present invention relates to a novel skin moisturizing composition and application thereof. Particularly, the present invention relates to an anhydrous composition of small-molecule polysaccharides and application thereof.

2. The Prior Art

Skin functions as the first barrier against the external damages from the environment, such as UV radiation, pathogens, friction. From outside to the inside, skin contains the layer of epidermis, which consists of sebum, the horny layer, the granular layer, and the basal layer, the layer of dermis, which primarily consists of the connective tissue, and the hypodermis. With age, skin shows signs of aging, including wrinkles, fine lines, laxity, and sunken cheeks. The development of these signs of aging on skin results from many factors, for example, a lack of hyaluronic acid (abbreviated as HA), and deficiency in collagen. Among these factors, a lack of HA causes a decrease in skin hydration level, and leads to a decrease in skin plumpness and elasticity.

Hyaluronic acid, also termed hyaluronan or hyaluronate, is an essential component of the cellular matrix. HA in skin is mainly localized to the dermis and is able to retain water. This characteristic of water retainment comes from the ability of HA to hold high levels of water, which is up to 1000 ml water for 1 g of HA. HA is a polymer of disaccharides, with the disaccharide unit being glucuronic acid and acetyl-glucosamine. In a human body, the molecular weight of a hyaluronic acid molecule is about 5 kDa to 10 MDa.

To resolve the aforementioned issues of a lack of HA and decreased skin hydration level with age, a variety of products for moisturizing skin have been sold in the market, most of which are hydrous products containing high molecular weight HA with a molecular weight of millions of Dalton. Topical administration of these products onto the skin may increase moisture of the skin surface and prevent water loss from the skin towards the environment, an effect called barrier for moisture-lock. Recently, skin care products manufacturers have also developed hydrous products for moisturization containing small-molecule HA, with a molecular weight from 10 kDa to lower than 1 MDa, to enhance skin absorption of HA and thus to promote the ability of skin to retain water. However, this attempt is of little success.

The limited moisturizing effect of the marketed products containing small-molecule HA may be due to two reasons. First is the inferior quality of small-molecule HA. The second reason is the formulations of the moisturizing products containing small-molecule HA. The methods for industrial preparation of small-molecule HA are mostly chemical degradation, which breaks high molecular weight HA into small-molecule HA by acid degradation, alkaline degradation, or oxidative degradation. This preparation is simple, but the molecular size of the resulting small-molecule HA is usually irregular or the molecular structure is destroyed, leading to a lowered effective concentration of the small-molecule HA capable of penetrating the gap (about 40-50 nm) between keratinocytes in the horny layer of skin, or less water absorption by the small-molecule HA. These in turn affect the effect of the moisturizing products containing small-molecule HA.

Regarding the formulations of the moisturizing products containing small-molecule HA, because all marketed HA products for moisturization contain water, and the swelling property of HA causes enlargement in the size of the small-molecule HA, this enlarged size in turn hinders the penetration of the small-molecule HA across the horny layer of skin.

Therefore, there is a need to develop a novel anhydrous composition comprising small-molecule HA of regular size and structural integrity, allowing its effective penetration across the horny layer of skin and effectively increasing skin hydration level. Furthermore, other polysaccharides that absorb and retain water may be used in this novel formulation of the anhydrous composition for development of novel skin moisturizing products.

SUMMARY OF THE INVENTION

The present invention provides an anhydrous composition of small-molecule polysaccharides, consisting of at least a small-molecule polysaccharide and an anhydrous base, wherein the small-molecule polysaccharide has a molecular size of about 12-22 nm and directly penetrates the horny layer of skin.

In one embodiment of the present invention, the small-molecule polysaccharide is a small-molecule hyaluronic acid, which is obtained by hydrolysis of a hyaluronic acid by a hyaluronidase and has a molecular weight ranging from 4 kDa to 8 kDa.

In one preferred embodiment of the present invention, the small-molecule hyaluronic acid is at a concentration from 0.5% w/v to 3% w/v, based on a total volume of the anhydrous composition of small-molecule polysaccharides.

In one embodiment of the present invention, the anhydrous base is at least a polyol.

In another aspect, the present invention also provides a method of effectively maintaining skin hydration level in a subject in need thereof, comprising administering to the subject an anhydrous composition of small-molecule polysaccharides, wherein the anhydrous composition of small-molecule polysaccharides consists of at least a small-molecule polysaccharide and an anhydrous base, and the small-molecule polysaccharide has a molecular size of 12-22 nm and directly penetrates the horny layer of skin.

In one embodiment of the present invention, the small-molecule polysaccharide is a small-molecule hyaluronic acid, which is obtained by hydrolysis of a hyaluronic acid by a hyaluronidase and has a molecular weight ranging from 4 kDa to 8 kDa.

In one preferred embodiment of the present invention, the small-molecule hyaluronic acid is at a concentration from 0.5% w/v to 3% w/v, based on a total volume of the anhydrous composition of small-molecule polysaccharides.

In one embodiment of the present invention, the anhydrous base is at least a polyol.

The formulation of the anhydrous composition of small-molecule polysaccharides provided in the present invention allows the small-molecule polysaccharide to maintain a molecular size of 12-22 nm, precluding an increased molecular size of over 40-50 nm, the size of the gap between keratinocytes in the horny layer of skin, caused by absorption of water from the composition and enlargement of the small-molecule polysaccharides. As a result, the small-molecule polysaccharide can penetrate directly across the horny layer of skin and effectively retain water in the epidermis of skin. The transdermal absorption characteristic of the anhydrous composition of small-molecule polysaccharides provided in the present invention not only promotes the ability of skin to retain water, but also maintains skin hydration level for long time, leading to effective prevention of or improvement in wrinkle formation, skin laxity, or sunken skin.

All of the currently marketed hyaluronic acid (HA) products for moisturization contain high levels of water. The use of water as a main solvent has brought convenience to the production process, because HA is highly hydrophilic and is easy to dissolve in water in a step of stirring during the production process. Instead, in one embodiment of the present invention, polyols are utilized as the solvent to create an anhydrous environment, allowing the small-molecule HA to retain its transdermal absorption characteristic and thus fully exerts its effect on moisturizing skin. Moreover, polyols are good carriers for skin delivery and are able to create conditions that favor skin delivery. In addition, polyols exhibit excellent antibacterial effect Polysaccharides materials such as HA provide a suitable habitat for microorganisms to grow. An even better habitat for microorganisms is provided when the polysaccharides are mixed with water. Thus, it is necessary for the marketed HA products to include additional antiseptics or to be subjected to a sterilization treatment. However, when high concentrations of polyols are used as the anhydrous base in the preset invention, no additional addition of antiseptics or a further sterilization procedure is required due to the excellent antibacterial effect of polyols.

The present invention is further explained in the following drawings and examples. It is understood that the examples given below do not limit the scope of the invention, and it will be evident to those skilled in the art that modifications can be made without departing from the scope of the appended claims.

BRIEF DESCRIPTION OF THE DRAWINGS

The present invention will be apparent to those skilled in the art from the following detailed description of the preferred embodiments, with reference to the attached drawings, in which.

DETAILED DESCRIPTION OF THE PREFERRED EMBODIMENT

The anhydrous composition of small-molecule polysaccharides provided in the present invention is further described in the following examples. In one preferred embodiment of the present invention, a small-molecule polysaccharide selected for exemplification is small-molecule hyaluronic acid (small-molecule HA). First, anhydrous compositions of small-molecule HA at specific concentrations were prepared from the small-molecule HA and polyols that were used as an anhydrous base. The compositions were then topically applied to the skin to evaluate the promoting effects of the anhydrous compositions of small-molecule HA on skin hydration level. Also, the compositions were then topically applied to the skin to analyze the effects of the anhydrous compositions of small-molecule HA on skin elasticity and skin hydration level.

Definition

As used herein, the terms "hyaluronic acid" and the abbreviation of "HA" refer to hyaluronic acid with a molecular weight of above about 1 MDa, salts thereof, or their derivatives; these terms are interchangeable with the term "high molecular weight hyaluronic acid" and the abbreviation of "high molecular weight HA" in order to be distinguished from the small-molecule hyaluronic acid used in the specification of the present invention.

Unless the molecular weight is otherwise specified, the terms "small-molecule hyaluronic acid" and the abbreviation of "small-molecule HA" in the present invention refer to hyaluronic acid with a molecular weight of about 4 kDa to about 8 kDa, salts thereof, or their derivatives. The small-molecule HA contains about 12-22 disaccharide units and have a molecular size of about 12-22 nm.

As used herein, the term "polysaccharides" refers to polymers of sugars and slats thereof which have high water absorption capability and form through dehydration polymerization of multiple monosaccharides, derivatives of monosaccharides, disaccharides, or derivatives of disaccharides, with the component monosaccharides or derivatives of monosaccharides for a polysaccharide being of one or multiple types. For example, hyaluronic acid, glucan, aloe polysaccharides, seaweed polysaccharides, Tremella polysaccharides, and *Ganoderma* polysaccharides, each of which can be applied for moisturizing effect.

As used herein, the term "small-molecule polysaccharides" refers to the aforementioned polysaccharides or their hydrolysates which have a molecular size of about 12-22 nm.

As used herein, the term "polyols" refers to alcohols with more than two hydroxyl groups, such as ethylene glycol, glycerol (also called glycerine), propylene glycol, butanediols, hexane-hexol (also called sorbitol). All polyols used for preparation of the anhydrous compositions of small-molecule HA of the present invention are in the anhydrous form.

Methods and Materials

Anhydrous Composition of Small-Molecule HA

The anhydrous compositions of small-molecule HA in the following examples contained small-molecule HA that were purchased from Bloomage Freda Biopharm Co., Ltd. (China). The small-molecule HA called Mini HA is produced by hyaluronidase-catalyzed hydrolysis of high molecular weight HA at 30-50° C. and at neutral pH, and it is in the form of anhydrous dry powder. Unless the molecular weight is otherwise specified, the small-molecule HA in the examples has a molecular weight of about 4 kDa to about 8 kDa and a molecular size of about 12-22 nm, and it consists of 12-22 disaccharide units of glucuronic acid and acetyl-glucosamine. For preparation of the anhydrous compositions of small-molecule HA, which was carried out at room temperature below 40° C. and at a relative humidity of 45%±5%, the dry powder of small-molecule HA was first mixed thoroughly with anhydrous propylene glycol in a vacuum mixer, and then anhydrous glycerol was added to the mixture and the mixing was continued till the powder was fully dissolved. Anhydrous compositions of small-molecule HA at a weight/volume concentration of 2% w/v were prepared accordingly, and the compositions contained 58% propylene glycol and 40% glycerol. All the concentrations of the anhydrous compositions of small-molecule HA mentioned in the following examples are the weight/volume concentrations (w/v) of small-molecule HA in the compositions. To maintain the anhydrous state of the anhydrous compositions of small-molecule HA, all containers and contacting tools were kept dry in the preparation process, and the anhydrous compositions of small-molecule HA were filled into vacuum bottles through a vacuum filler for storage.

Anhydrous Composition of Barrier HA

According to the method of preparing the anhydrous composition of small-molecule HA, the anhydrous composition of barrier HA in the following examples was prepared from the anhydrous dry powder of high molecular weight HA (with a HA molecular weight of about 1 MDa) purchased from Bloomage Freda Biopharm Co., Ltd. (China). The anhydrous composition of barrier HA was at a weight/volume concentration of 1% w/v, and this composition contained 59% propylene glycol and 40% glycerol. All the concentrations of the anhydrous composition of barrier HA mentioned in the following examples are the weight/volume concentrations (w/v) of barrier HA in the composition. To maintain the anhydrous state of the anhydrous composition of barrier HA, all containers and contacting tools were kept dry in the preparation process, and the anhydrous composition of barrier HA was filled into vacuum bottles through a vacuum filler for storage.

Hydrous Small-Molecule HA Sample

The hydrous small-molecule HA samples in the following examples were prepared by mixing the powder of Mini HA (with a HA molecular weight of about 4 kDa-8 kDa) purchased from Bloomage Freda Biopharm Co., Ltd. (China) with double deionized water. The small-molecule HA samples were at a weight/volume concentration of 2% w/v, and the samples contained 98% water, mimicking the marketed hydrous HA products containing 1% HA and more than 80% water. All the concentrations of the small-molecule HA samples mentioned in the following examples are the weight/volume concentrations (w/v) of small-molecule HA in the samples.

Hydrous HA Sample

The hydrous HA samples in the following examples were prepared by mixing the powder of HA (with a HA molecular weight of about 1 MDa) purchased from Bloomage Freda Biopharm Co., Ltd. (China) with double deionized water. The HA samples were at a weight/volume concentration of 2% w/v, and the samples contained 98% water, mimicking the marketed hydrous HA products containing 1% HA and more than 80% water. All the concentrations of the HA samples mentioned in the following examples are the weight/volume concentrations (w/v) of HA in the samples.

In Vitro Transdermal Delivery Analysis

First, a permeable membrane, the epidermis of pig ear skin in this experiment, was prepared. The surface of pig ear skin was washed with double deionized water, and the epidermis of pig ear skin was separated with a scalpel and cut to form a permeable membrane with an area of 1.5×1.5 cm$^2$ and a width of 650 μm. Next, the permeable membrane was soaked in phosphate buffered saline (abbreviated as PBS), packed into bag, and frozen for next time use. Prior to the experiment, a permeable membrane was thawed to room temperature by soaked in PBS for keratinocytes to return to their natural states, and then the membrane was fixed onto the Franz type diffusion cell (LOGAN FDC-6, U.S.; with a permeation area of 0.636 cm$^2$). To verify the integrity of the permeable membrane, the upper and lower parts of the diffusion cell were first filled with PBS. After bubbles were removed from the cell, the resistance across the permeable membrane was measured to be greater than 4kΩ, indicating the epidermis of skin was fine and flawless. When the in vitro transdermal delivery analysis was carried out, 1.0 mL of the sample to be measured was placed into the donor chamber at the upper part of the diffusion cell, the PBS solution was filled into the receptor chamber at the lower part (with a volume of 5.3 mL), and the heater circulator (VTC-200, U.S.) was turned on. The concentration distribution in the receptor chamber for the sample to be measured was balanced using a stirbar. For the following quantitative analysis utilizing high performance liquid chromatography (HPLC), a sampling of 50 μL from the receptor chamber was performed for every time interval and a same volume of PBS solution was refilled to maintain the solution volume in the receptor chamber. For each experiment, 5 measurements were made using 5 diffusion cells simultaneously to obtain an average. The HPLC consists of a TYPE BETA 50 GRADIENT pump (ECOMSRO, Czech), a SPD-10Avp UVVIS detector (Shimadzu, Japan), a DG1310 On-line degasser (Uniflows, Japan), and a MetaChem Polaris C18-A (5 μm, 150×4.6 mm) column (Agilent Technologies, U.S.). For sample analysis, isocratic elution using 5 mM NaH$_2$PO$_4$ buffer (pH 3.0) was performed with a flow rate of 1.0 mL/min, and the detection wavelength was 260 nm. The concentration of the sample was calculated based on a calibration curve made from AA2G standard solutions at concentrations of 10 ppm-200 ppm. The concentration of each sample was the mean of triplicate measurements.

Skin Hydration Level Test

Skin hydration level was measured by the skin hydration measuring devices, either Skicon 200 (Acaderm) or Corneometer® CM 825 (Courage+Khazaka electronic GmbH). In the test process, the probe connected to the skin hydration measuring device was put onto a participant's skin area to be measured, and the hydration level of the skin surface was determined. The two skin hydration measuring devices are both able to measure skin moisture content. For Skicon 200, the hydration level of skin surface is determined based on the conductance of the skin area to be measured; for Corneometer® CM 825, the hydration level of skin surface is determined based on the capacitance change of the electrode on the surface of the probe. The results of the measurement were used further to calculate the percent change in hydration level of skin surface. Because skin hydration level is affected by external factors such as temperature and humidity, a test is carried out only after the participants has been in a constant temperature and humidity room for 20 min of balancing. The environmental conditions for the test were a temperature of 20° C.±1° C. and a relative humidity of 50%±5%.

Skin Elasticity Test

Skin elasticity was measured by the skin elasticity measuring device, Cutometer MPA 580 (Courage+Khazaka electronic GmbH). In the test process, the skin elasticity probe connected to the skin elasticity measuring device was put onto a participant's skin area to be measured to suck up the area by negative pressure applied onto the skin surface, and to measure the change in the penetration depth of the area to be measured over time. The results of the measurements were then processed by the accompanied software of the skin elasticity measuring device to generate the skin elasticity index. These data were used further to calculate the percent change in skin elasticity. Because skin elasticity is affected by external factors such as temperature and humidity, a test is carried out only after the participants has been in a constant temperature and humidity room for 10 min of balancing. The environmental conditions for the test were a temperature of 20° C.±1° C. and a relative humidity of 50%±5%.

Prior to the aforementioned skin hydration level test and skin elasticity test, the participant's skin areas to be measured were first washed and dried. Next, the aforementioned tests were carried out after application of the various HA or small-molecule HA samples.

Example 1

The Effective Penetration of the Small-Molecule HA in the Anhydrous Composition of Small-Molecule HA Across the Horny Layer of Skin and the Epidermis To verify the formulation of the anhydrous composition of small-molecule HA of the present invention allows the small-molecule HA to penetrate the horny layer of skin and the epidermis more effectively when compared with the hydrous formulation for general hydrous HA products, the epidermis of pig ear skin was used for in vitro transdermal delivery analysis in this example. At 43° C., the diffusion rates across the epidermis were compared between the small-molecule HA, with a molecular weight of 4 kDa-8 kDa, in the 2% anhydrous composition of small-molecule HA and the small-molecule HA, with a molecular weight of 4 kDa-8 kDa, in the 2% hydrous small-molecule HA sample.

The above mentioned anhydrous composition of small-molecule HA or the hydrous small-molecule HA sample was added to the donor chamber of the diffusion cell, and triplicate samplings from the receptor chamber were carried out within 1 hr for HPLC quantification. The result from the quantification was divided by the permeation area of the diffusion cell to obtain the cumulative amount of small-molecule HA diffused per unit area. According to the following equation:

$$J=dQ/dt$$

The diffusion rate (J in the equation) across the epidermis for small-molecule HA is calculated as the time (t in the equation) differentiation of the cumulative amount diffused per unit area (Q in the equation).

The experimental results showed that the diffusion rate across the epidermis for the small-molecule HA in the anhydrous composition of small-molecule HA of the present invention was 217.86 µg/cm$^2$·hr, which was significantly higher than the value of 156.02 µg/cm$^2$·hr, the diffusion rate across the epidermis for the small-molecule HA in the hydrous small-molecule HA sample. Thus, the anhydrous composition of small-molecule HA of the present invention allows the small-molecule HA to penetrate the horny layer of skin and the epidermis more effectively.

Example 2

The Effects of Water and the Molecular Weight of HA on the Ability of HA Compositions to Retain Water in Skin To evaluate the effect of the formulation of the anhydrous composition of small-molecule HA of the present invention and the effect of the molecular weight of small-molecule HA on the ability of the composition to retain water in skin, the followings were first prepared: mixing double deionized water or a mixture of propylene glycol and glycerol with HA having a molecular weight of 1,700 kDa-1,800 kDa or 1,000 kDa-1,100 kDa or with small-molecule HA having a molecular weight of 110 kDa-120 kDa or 4 kDa-8 kDa to produce 2% hydrous HA samples containing 1,700 kDa-1,800 kDa or 1,000 kDa-1,100 kDa HA, 2% hydrous small-molecule HA samples containing 110 kDa-120 kDa or 4 kDa-8 kDa HA, 2% anhydrous HA samples (comprising 58% propylene glycol and 40% glycerol) containing 1,700 kDa-1,800 kDa or 1,000 kDa-1,100 kDa HA, and 2% anhydrous composition of small-molecule HA (comprising 58% propylene glycol and 40% glycerol) containing 110 kDa-120 kDa or 4 kDa-8 kDa HA. Next, the four hydrous HA samples or hydrous small-molecule HA samples, containing HA with different molecular weights, were applied to four skin areas respectively on the right forearms of three participants at the age of 25-35, and the other four anhydrous HA samples or anhydrous compositions of small-molecule HA, containing HA with different molecular weights, were also applied to four skin areas respectively on the left forearms of the same participants. Each skin area was 4×4 cm$^2$; and the amount of application was 3.0±0.1 mg/cm$^2$. The skin hydration level of the applied skin area was measured using the skin hydration measuring device Corneometer CM 825 (Courage+Khazaka electronic GmbH) prior to and 1 hr, 2 hr, 4 hr, 6 hr, and 8 hr after the application.

Figure 1A:
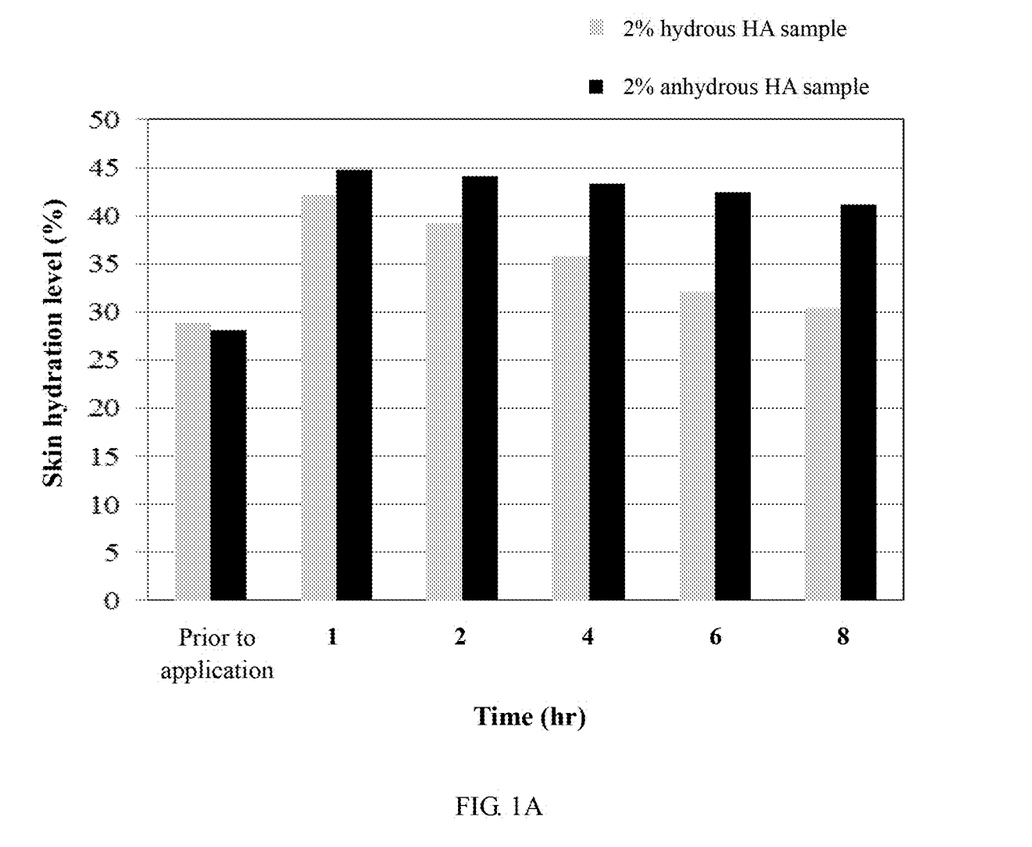
FIG. 1A shows the change in the hydration level of skin after application of the hydrous hyaluronic acid (HA) sample or the anhydrous HA sample to the skin, with the two samples containing 1,700 kDa-1,800 kDa HA.
Figure 1B:
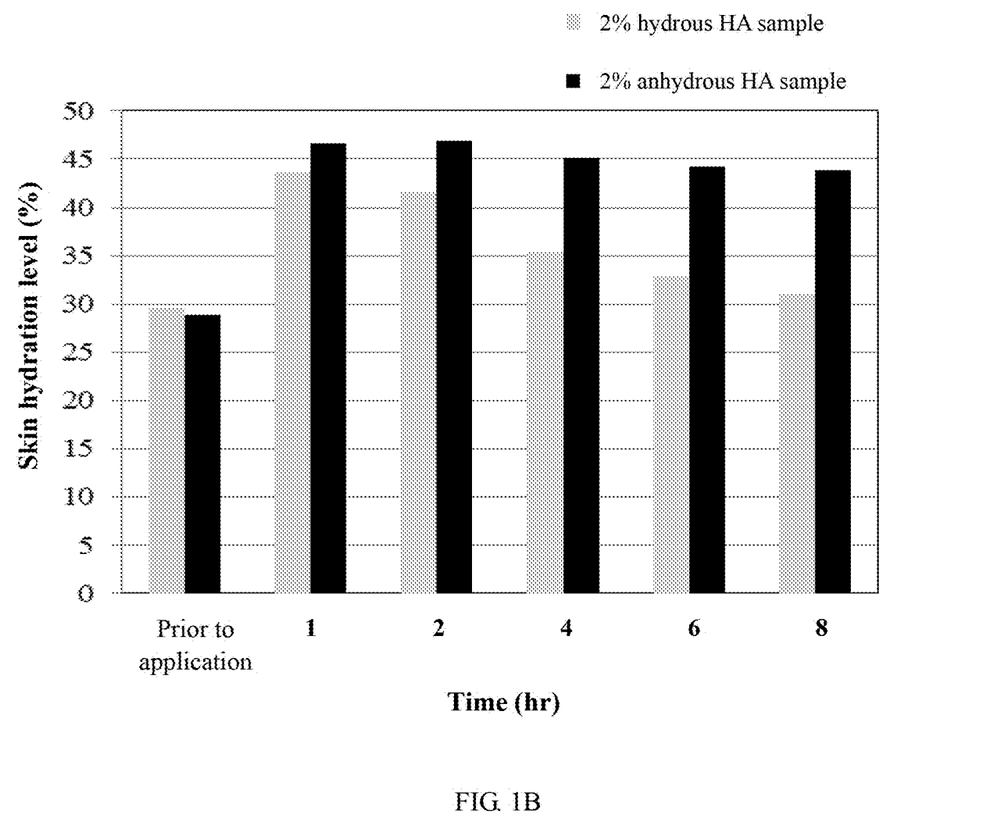
FIG. 1B shows the change in the hydration level of skin after application of the hydrous HA sample or the anhydrous HA sample to the skin, with the two samples containing 1,000 kDa-1,100 kDa HA.
Figure 1C:
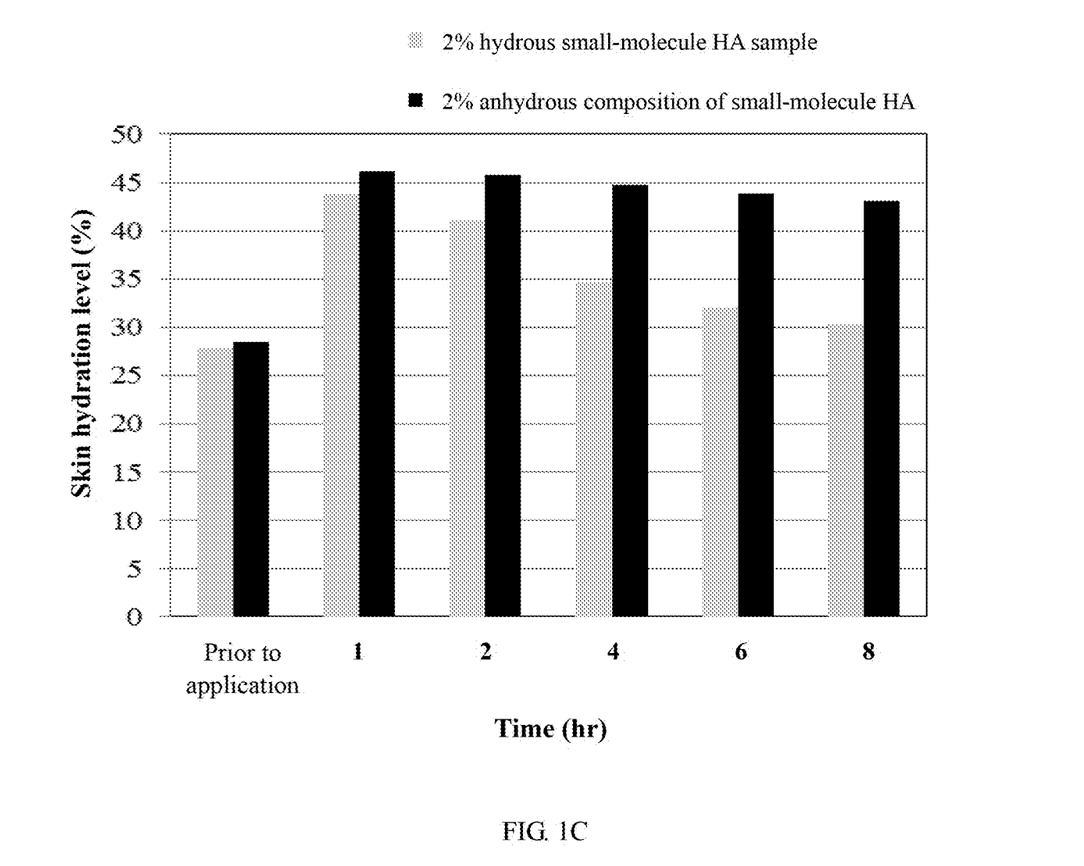
FIG. 1C shows the change in the hydration level of skin after application of the hydrous small-molecule HA sample or the anhydrous composition of small-molecule HA to the skin, with both the sample and the composition containing 110 kDa-120 kDa HA.
Figure 1D:
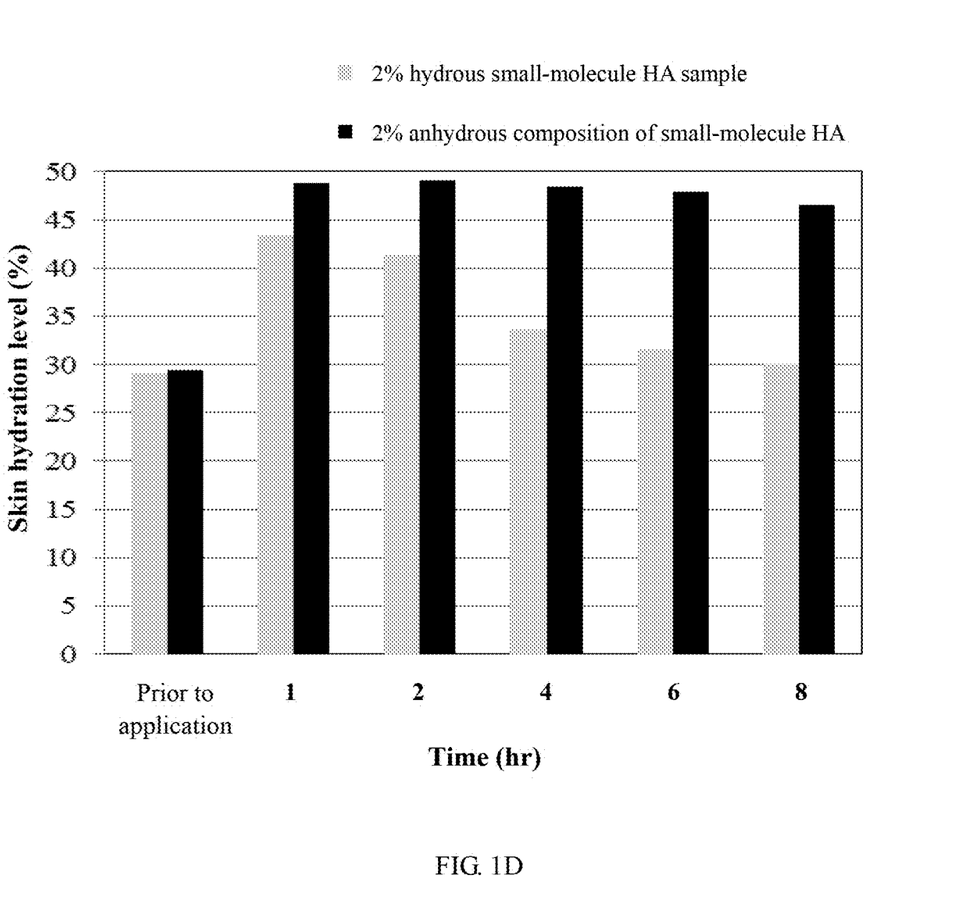
FIG. 1D shows the change in the hydration level of skin after application of the hydrous small-molecule HA sample or the anhydrous composition of small-molecule HA of the present invention to the skin, with both samples containing 4 kDa-8 kDa HA.
Figure 1E:
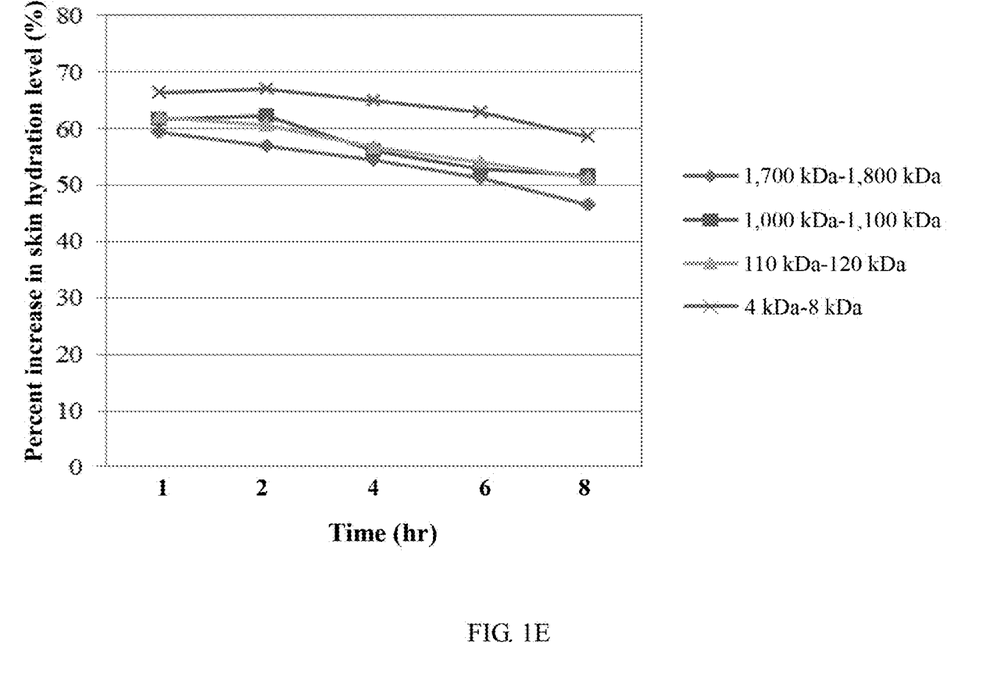
FIG. 1E shows the percent increase in the hydration level of skin according to FIGS. 1A-1D after application of the anhydrous HA samples or the anhydrous compositions of small-molecule HA to the skin.

The experimental results are shown in FIGS. 1A-D and they prove that the presence or absence of water in the sample and the molecular weight of HA both affected the skin hydration level of the applied skin area. In FIGS. 1A-D, the horizontal coordinate represents time (hr), the longitudinal coordinate represents the skin hydration level (%), and the values for each bar represent the mean values of the skin hydration level of the three participants and they are also shown in TABLEs 1-4. During the time interval from 1 hr to 8 hr after the application, no matter for what molecular weight of HA, the hydration level of skin after application of the anhydrous HA samples or the anhydrous compositions of small-molecule HA was higher and the decrease in the hydration level over time was slower when compared with those of skin after application of hydrous HA samples or hydrous small-molecule HA samples. In other words, the anhydrous formulation of HA compositions exhibits better ability to retain water for a longer period of time. In addition, the skin hydration level prior to the application was used as the reference to calculate the percent increase in the hydration level of skin after application of the anhydrous HA samples or the anhydrous compositions of small-molecule HA, each of which contained HA with different molecular weights. As shown in TABLE 5 and FIG. 1E, the anhydrous composition of small-molecule HA which contains small-molecule HA with a molecular weight of 4 kDa-8 kDa possesses the best capability to moisturize skin for the longest period of time. Therefore, this example proves that anhydrous formulation and the small-molecule HA which is at a molecular weight of 4 kDa-8 kDa can effectively enhance the ability of HA compositions to retain water in skin and extend the moisturizing effect.

TABLE 1

Results of the skin hydration level test for the hydrous HA sample and the anhydrous HA sample, with the two samples containing 1,700 kDa-1,800 kDa HA

| | Skin hydration level at different time points prior to and after application (%) | | | | | |
|---|---|---|---|---|---|---|
| | Prior to application | 1 hr | 2 hr | 4 hr | 6 hr | 8 hr |
| 2% hydrous HA sample | 28.9 | 42.2 | 39.3 | 35.8 | 32.1 | 30.4 |
| 2% anhydrous HA sample | 28.1 | 44.8 | 44.1 | 43.4 | 42.5 | 41.2 |

TABLE 2

Results of the skin hydration level test for the hydrous HA sample and the anhydrous HA sample, with the two samples containing 1,000 kDa-1,100 kDa HA

| | Skin hydration level at different time points prior to and after application (%) | | | | | |
|---|---|---|---|---|---|---|
| | Prior to application | 1 hr | 2 hr | 4 hr | 6 hr | 8 hr |
| 2% hydrous HA sample | 29.7 | 43.6 | 41.7 | 35.4 | 32.9 | 31.1 |
| 2% anhydrous HA sample | 28.9 | 46.7 | 46.9 | 45.1 | 44.2 | 43.8 |

TABLE 3

Results of the skin hydration level test for the hydrous small-molecule HA sample and the anhydrous composition of small-molecule HA, with both the sample and the composition containing 110 kDa-120 kDa HA

| | Skin hydration level at different time points prior to and after application (%) | | | | | |
|---|---|---|---|---|---|---|
| | Prior to application | 1 hr | 2 hr | 4 hr | 6 hr | 8 hr |
| 2% hydrous small-molecule HA sample | 27.8 | 43.9 | 41.1 | 34.6 | 32.1 | 30.3 |
| 2% anhydrous composition of small-molecule HA | 28.5 | 46.2 | 45.8 | 44.7 | 43.9 | 43.1 |

TABLE 4

Results of the skin hydration level test for the hydrous small-molecule HA sample and the anhydrous composition of small-molecule HA, with both the sample and the composition containing 4 kDa-8 kDa HA

| | Skin hydration level at different time points prior to and after application (%) | | | | | |
|---|---|---|---|---|---|---|
| | Prior to application | 1 hr | 2 hr | 4 hr | 6 hr | 8 hr |
| 2% hydrous small-molecule HA sample | 29.1 | 43.4 | 41.5 | 33.6 | 31.6 | 30.1 |
| 2% anhydrous composition of small-molecule HA | 29.4 | 48.9 | 49.1 | 48.5 | 47.9 | 46.6 |

TABLE 5

The effect of the molecular weight (MW) of HA on the percent increase in the skin hydration level

| 2% anhydrous HA sample or 2% anhydrous composition of small-molecule HA | Percent increase in the skin hydration level at different time points after application (%) | | | | |
|---|---|---|---|---|---|
| | 1 hr | 2 hr | 4 hr | 6 hr | 8 hr |
| MW 1,700 kDa-1,800 kDa | 59.43 | 56.94 | 54.45 | 51.25 | 46.62 |
| MW 1,000 kDa-1,100 kDa | 61.59 | 62.28 | 56.06 | 52.94 | 51.56 |
| MW 110 kDa-120 kDa | 62.11 | 60.70 | 56.84 | 54.04 | 51.23 |
| MW 4 kDa-8 kDa | 66.33 | 67.01 | 64.97 | 62.93 | 58.50 |

Example 3

The Effect of Concentration of the Anhydrous Composition of Small-Molecule HA on its Ability to Retain Water in Skin To evaluate the ability of different concentrations of the anhydrous composition of small-molecule HA of the present invention to retain water in skin, the small-molecule HA with a molecular weight of 4 kDa-8 kDa was first used to prepare the anhydrous compositions of small-molecule HA at the concentrations of 0.1%, 0.5%, 1.0%, 2.0%, and 3.0%. These compositions contained 59.9%, 59.5%, 59%, 58%, or 57% propylene glycol respectively, and they all contained 40% glycerol. The aforementioned five anhydrous compositions of small-molecule HA at different concentrations were then applied to five skin areas respectively on the right and left forearms of five participants at the age of 30-45. Each skin area was 4×4 cm$^2$; and the amount of application was 3.0±0.1 mg/cm$^2$. The skin hydration level of the applied skin area was measured using the skin hydration measuring device Corneometer CM 825 (Courage+Khazaka electronic GmbH) prior to and 1 hr, 2 hr, 4 hr, 6 hr, and 8 hr after the application.

Figure 2:
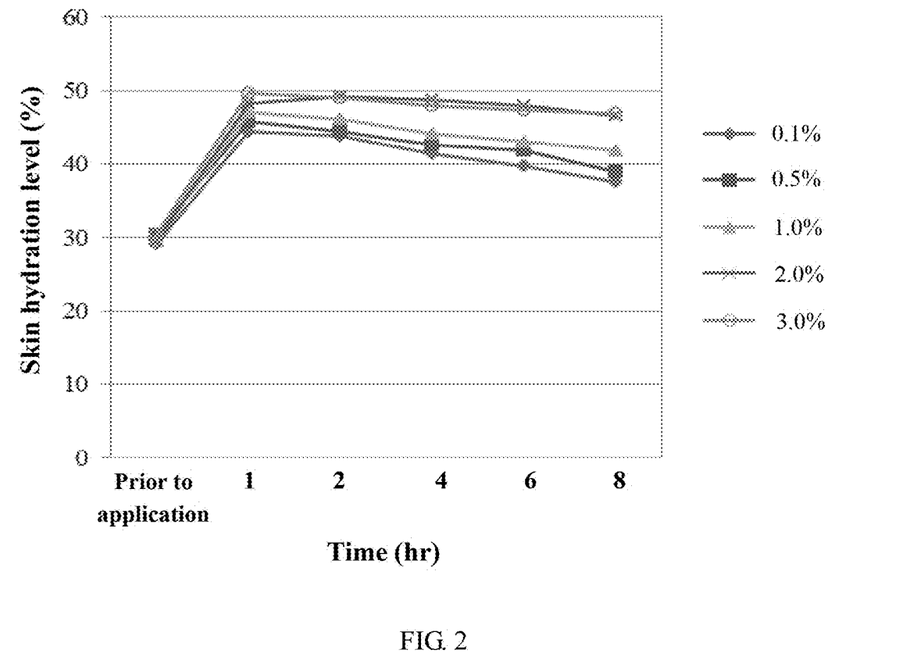
FIG. 2 shows the change in the hydration level of skin after application of different concentrations of the anhydrous compositions of small-molecule HA of the present invention to the skin.

As shown in FIG. 2, the concentration of the anhydrous composition of small-molecule HA affected the skin hydration level of the applied skin area. In FIG. 2, the horizontal coordinate represents time (hr), the longitudinal coordinate represents the skin hydration level (%), and the values for each point represent the mean values of the skin hydration level of the five participants and they are also shown in TABLE 6. As the concentration of the small-molecule HA in the anhydrous composition of small-molecule HA increased from 0.5% to 2%, the skin hydration level of the applied skin area of the participants also increased. However, when the concentration of the anhydrous composition of small-molecule HA reached 3%, the skin hydration level of the applied skin area did not increase significantly and it was around the same as that of the skin area after application of the 2% anhydrous composition of small-molecule HA. Thus, the anhydrous composition of small-molecule HA at a concentration of 2% is sufficient to exhibits the best ability to retain water in skin.

TABLE 6

The effect of concentration of the anhydrous composition of small-molecule HA on the skin hydration level

| Anhydrous composition of small-molecule HA | Skin hydration level at different time points prior to and after application (%) | | | | | |
|---|---|---|---|---|---|---|
| | Prior to application | 1 hr | 2 hr | 4 hr | 6 hr | 8 hr |
| 0.1% | 29.1 | 44.5 | 43.9 | 41.3 | 39.7 | 37.5 |
| 0.5% | 30.4 | 45.8 | 44.5 | 42.6 | 41.8 | 38.9 |
| 1.0% | 29.6 | 47.1 | 46.2 | 44.2 | 43.1 | 41.9 |
| 2.0% | 29.5 | 48.3 | 49.2 | 48.7 | 47.9 | 46.6 |
| 3.0% | 30.3 | 49.6 | 49.1 | 47.9 | 47.4 | 46.9 |

Example 4

Test for the Long-Term Ability of the Anhydrous Composition of Small-Molecule HA to Retain Water in Skin To evaluate the long-term ability of the anhydrous composition of small-molecule HA to retain water in skin, the 2% hydrous HA sample and the 2% anhydrous composition of small-molecule HA were respectively applied to a skin area on the left forearms and a skin area on the right forearms of 10 participants at the age of 20-50 twice a day. Each skin area was 4×4 cm$^2$; the amount of application was 3.0±0.1 mg/cm$^2$; and the application was continued for 8 weeks. The skin hydration level of the applied skin area was measured using the skin hydration measuring device Corneometer CM 825 (Courage+Khazaka electronic GmbH) prior to and 1 week, 2 weeks, 4 weeks, 6 weeks, and 8 weeks after the application.

Figure 3:
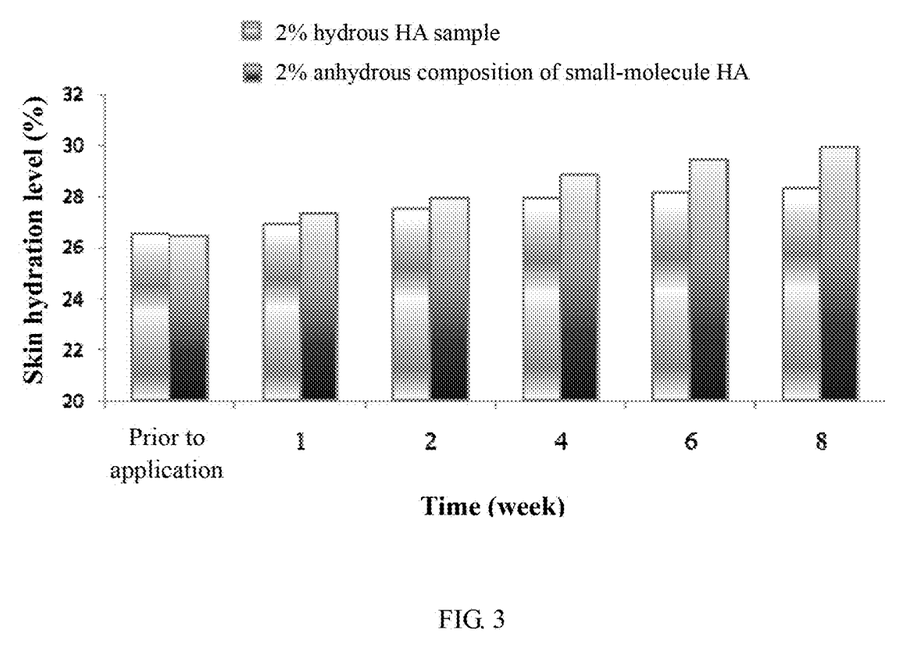
FIG. 3 shows the change in the hydration level of skin after long-term application of the anhydrous composition of small-molecule HA of the present invention to the skin.

FIG. 3 shows the change in the hydration level of skin after long-term application of the anhydrous composition of small-molecule HA of the present invention. In FIG. 3, the horizontal coordinate represents time (week), the longitudinal coordinate represents the skin hydration level (%), and the values for each bar represent the mean values of the skin hydration level of the ten participants. When the anhydrous composition of small-molecule HA of the present invention was continually applied to the participants for 8 weeks, their skin hydration level increased by 27%, compared to the hydration level of skin prior to the application. Besides, the moisturizing effect of the anhydrous composition of small-molecule HA was significantly better than that of the hydrous HA sample.

The generally marketed hydrous HA products mostly contain high molecular weight HA to prevent water loss from skin surface, and may further comprise small-molecule HA in order to increase skin hydration level, based on the ability of small-molecule HA to penetrate into the skin. To further validate only the separate use of small-molecule HA and high molecular weight HA allows an additive skin moisturizing effect, a first application of the anhydrous composition of small-molecule HA and a later application of the anhydrous composition of barrier HA to the skin surface are set as the experimental group in the following EXAMPLEs 5-7. The anhydrous composition of barrier HA contains HA with a molecular weight of about 1 MDa and thus is able to cover the skin surface to prevent water loss from the skin towards the environment.

Example 5

The Ability of the Combination of the Anhydrous Composition of Small-Molecule HA and the Anhydrous Composition of Barrier HA to Retain Water in Skin In this example, the effect of the first application of the anhydrous composition of small-molecule HA of the present invention and the later application of the anhydrous composition of barrier HA was compared with the effect of the application of the general hydrous HA products on the ability to retain water. The followings were first prepared: a 2% anhydrous composition of small-molecule HA, a 1% anhydrous composition of barrier HA, and a mixed anhydrous composition of 2% small-molecule HA and 1% barrier HA (consisting of 2% small-molecule HA, 1% barrier HA, 57% propylene glycol, and 40% glycerol). Next, the aforementioned compositions were applied according to the following four groups: (a) two times of application of the 1% anhydrous composition of barrier HA, with a time interval of 2 min; (b) two times of application of the 2% anhydrous composition of small-molecule HA, with a time interval of 2 min; (c) two times of application of the mixed anhydrous composition of 2% small-molecule HA and 1% barrier HA, with a time interval of 2 min; (d) the first application of the 2% anhydrous composition of small-molecule HA for one time and the later application of the 1% anhydrous composition of barrier HA for one time, with a time interval of 2 min. The aforementioned compositions were applied to four skin areas respectively on the left forearms of the three participants at the age of 25-35. Each skin area was 4×4 cm$^2$; and the amount of application was 3.0±0.1 mg/cm$^2$. The skin hydration level of the applied skin area was measured using the skin hydration measuring device Corneometer CM 825 (Courage+Khazaka electronic GmbH) prior to and 1 hr, 2 hr, 4 hr, 6 hr, and 8 hr after the application.

Figure 4:
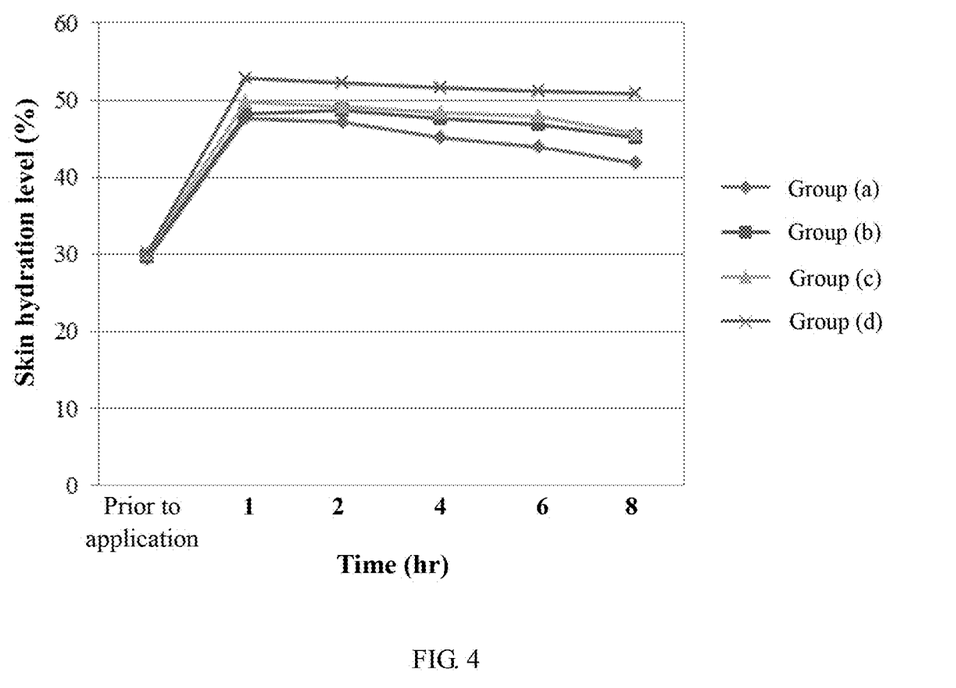
FIG. 4 shows change in the hydration level of skin after application of: (a) the anhydrous composition of small-molecule HA of the present invention; (b) the anhydrous composition of barrier HA; (c) the mixed anhydrous composition of small-molecule HA and barrier HA; (d) the combination of the anhydrous composition of small-molecule HA of the present invention and the anhydrous composition of barrier HA to the skin.

FIG. 4 shows the change in hydration level of skin after application according to the above mentioned four groups. In FIG. 4, the horizontal coordinate represents time (hr), the longitudinal coordinate represents the skin hydration level (%), and the values for each point represent the mean values of the skin hydration level of the three participants and they are also shown in TABLE 7. As shown in FIG. 4, when compared with two times of application of the mixed anhydrous composition of 2% small-molecule HA and 1% barrier HA, the first application of the 2% anhydrous composition of small-molecule HA and the later application of the 1% anhydrous composition of barrier HA resulted in significantly higher skin hydration level in the applied skin area. In addition, the experimental result also revealed that the first application of the anhydrous composition of small-molecule HA and the later application of the anhydrous composition of barrier HA led to a better skin moisturizing effect for a longer period of time, when compared with the single application of the anhydrous composition of small-molecule HA. In other words, administration of the combination of the anhydrous composition of small-molecule HA of the present invention and the anhydrous composition of barrier HA can cause an additive skin moisturizing effect, because of the characteristic of barrier HA to prevent water loss from the skin surface.

TABLE 7

The effect of the combination of the anhydrous composition of small-molecule HA and the anhydrous composition of barrier HA on the skin hydration level

| The four groups of application conditions | Skin hydration level at different time points prior to and after application (%) | | | | | |
|---|---|---|---|---|---|---|
| | Prior to application | 1 hr | 2 hr | 4 hr | 6 hr | 8 hr |
| Group (a) | 29.3 | 47.6 | 47.1 | 45.2 | 43.9 | 41.8 |
| Group (b) | 29.7 | 48.3 | 48.7 | 47.6 | 46.9 | 45.1 |
| Group (c) | 30.1 | 49.8 | 49.2 | 48.4 | 47.9 | 45.7 |
| Group (d) | 30.1 | 52.8 | 52.3 | 51.6 | 51.1 | 50.9 |

Example 6

Face Skin Elasticity Test for the Combination of the Anhydrous Composition of Small-Molecule HA and the Anhydrous Composition of Barrier HA To explore the mid to long-term effect of the combination of the anhydrous composition of small-molecule HA and the anhydrous composition of barrier HA, compared with general hydrous HA products, on the elasticity of face skin, the 2% hydrous HA sample and the combination of the 2% anhydrous composition of small-molecule HA and the 1% anhydrous composition of barrier HA were applied twice daily, in the morning and at night, for 14 days to the left face skin and the right face skin (including the skin area near the eye) of six participants respectively. The skin elasticity of the applied skin area was measured using the skin elasticity measuring device Cutometer MPA 580 (Courage+Khazaka electronic GmbH) at day 1 to 14 after the application. For the group in which the 2% anhydrous composition of small-molecule HA and the 1% anhydrous composition of barrier HA were applied, the 2% anhydrous composition of small-molecule HA was first applied to the right face once, and then the 1% anhydrous composition of barrier HA was applied to the right face once, with a time interval of 2 min. For the group in which only the 2% hydrous HA sample was applied, the sample was applied twice to the left face, with a time interval of 2 min.

Figure 5:
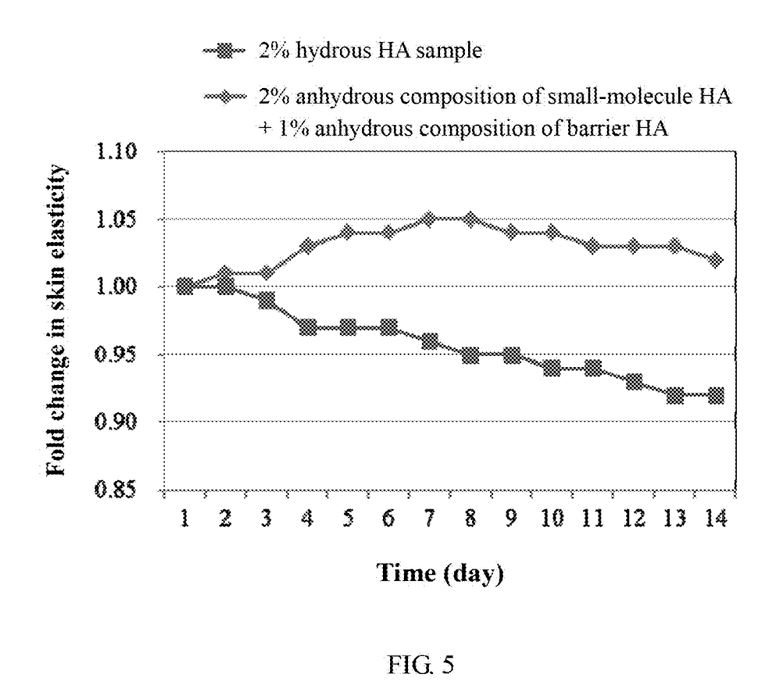
FIG. 5 shows the fold change in the elasticity of skin after application of the combination of the anhydrous composition of small-molecule HA of the present invention and the anhydrous composition of barrier HA to the skin.

FIG. 5 shows the change in the skin elasticity for the above mentioned two groups. In FIG. 5, the horizontal coordinate represents time (day), the longitudinal coordinate represents the fold change in the skin elasticity based on the measured skin elasticity at day 1, and the values of the fold change at each time point represent the mean values of the fold change in the skin elasticity of the six participants and they are also shown in TABLE 8. As shown in FIG. 5, in contrast to the reduced elasticity of face skin which the 2% hydrous HA sample was applied to, the elasticity of face skin increased when the combination of the 2% anhydrous composition of small-molecule HA and the 1% anhydrous composition of barrier HA was applied. In addition, this increased skin elasticity was effectively maintained for at least 14 days.

TABLE 8

The effect of different HA samples on the fold change in the skin elasticity

| | Fold change in the skin elasticity | |
|---|---|---|
| Time | 2% anhydrous composition of small-molecule HA + 1% anhydrous composition of barrier HA | 2% hydrous HA composition |
| Day 1 | 1.00 | 1.00 |
| Day 2 | 1.01 | 1.00 |
| Day 3 | 1.01 | 0.99 |
| Day 4 | 1.03 | 0.97 |
| Day 5 | 1.04 | 0.97 |
| Day 6 | 1.04 | 0.97 |
| Day 7 | 1.05 | 0.96 |
| Day 8 | 1.05 | 0.95 |
| Day 9 | 1.04 | 0.95 |
| Day 10 | 1.04 | 0.94 |
| Day 11 | 1.03 | 0.94 |
| Day 12 | 1.03 | 0.93 |
| Day 13 | 1.03 | 0.92 |
| Day 14 | 1.02 | 0.92 |

Example 7

The Ability of the Combination of the Anhydrous Composition of Small-Molecule HA and the Anhydrous Composition of Barrier HA to Retain Water in Skin To verify the mid to long-term ability of the combination of the anhydrous composition of small-molecule HA and the anhydrous composition of barrier HA, compared with general hydrous HA products, to retain water in skin, the 2% hydrous HA sample and the combination of the 2% anhydrous composition of small-molecule HA and the 1% anhydrous composition of barrier HA were applied twice daily, in the morning and at night, for 14 days to the left face skin and the right face skin (including the skin area near the eye) of six participants respectively. The skin hydration level of the applied skin area was measured using the skin hydration measuring device Skicon 200 (Acaderm) at day 1 to 14 after the application. For the group in which the 2% anhydrous composition of small-molecule HA and the 1% anhydrous composition of barrier HA were applied, the 2% anhydrous composition of small-molecule HA was first applied to the right face once, and then the 1% anhydrous composition of barrier HA was applied to the right face once, with a time interval of 2 min. For the group in which only the 2% hydrous HA sample was applied, the sample was applied twice to the left face, with a time interval of 2 min.

Figure 6:
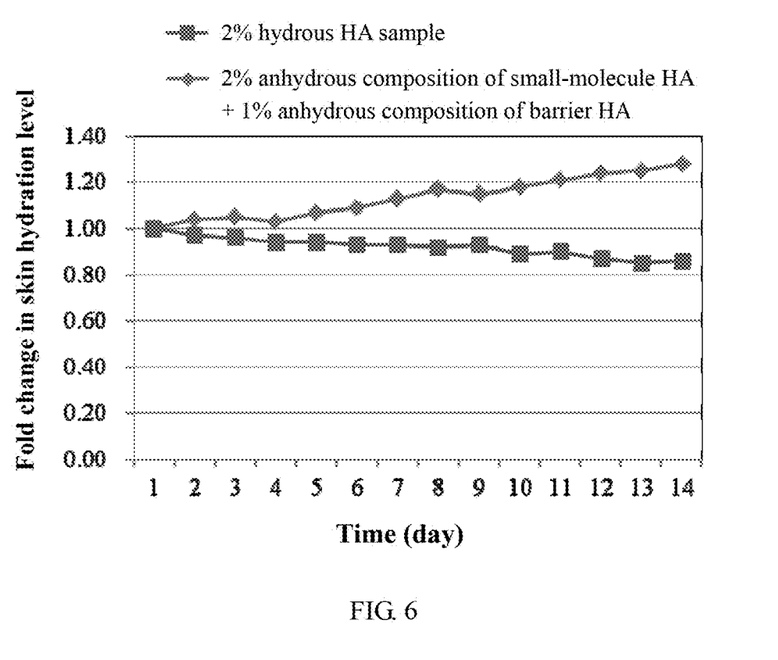
FIG. 6 shows the fold change in the hydration level of skin after application of the combination of the anhydrous composition of small-molecule HA of the present invention and the anhydrous composition of barrier HA to the skin.

FIG. 6 shows the change in the skin hydration level for the above mentioned two groups. In FIG. 6, the horizontal coordinate represents time (day), the longitudinal coordinate represents the fold change in the skin hydration level based on the measured skin hydration level at day 1, and the values of the fold change at each time point represent the mean values of the fold change in the skin hydration level of the six participants and they are also shown in TABLE 9. As shown in FIG. 6, in contrast to the reduced hydration level of face skin which the 2% hydrous HA sample was applied to, the hydration level of face skin increased when the combination of the 2% anhydrous composition of small-molecule HA and the 1% anhydrous composition of barrier HA was applied. Besides, the effect of this increased skin hydration level became more significant with time.

TABLE 9

The effect of different HA samples on the fold change in the skin hydration level

| | Fold change in the skin hydration level | |
|---|---|---|
| Time | 2% anhydrous composition of small-molecule HA + 1% anhydrous composition of barrier HA | 2% hydrous HA composition |
| Day 1 | 1.00 | 1.00 |
| Day 2 | 1.04 | 0.97 |
| Day 3 | 1.05 | 0.96 |
| Day 4 | 1.03 | 0.94 |
| Day 5 | 1.07 | 0.94 |
| Day 6 | 1.09 | 0.93 |
| Day 7 | 1.13 | 0.93 |
| Day 8 | 1.17 | 0.92 |
| Day 9 | 1.15 | 0.93 |
| Day 10 | 1.18 | 0.89 |
| Day 11 | 1.21 | 0.90 |
| Day 12 | 1.24 | 0.87 |
| Day 13 | 1.25 | 0.85 |
| Day 14 | 1.28 | 0.86 |

The currently marked moisturizing products containing small-molecule HA mostly further comprise high molecular weight HA, in order to achieve the effect of barrier for moisture-lock resulted from high molecular weight HA and the better ability of small-molecule HA to penetrate the skin at the same time. However, because of the attraction between the two types of molecules, the presence of high molecular weight HA would interfere with the penetration of small-molecule HA across the horny layer of skin and reduce the ability of small-molecule HA to retain water in skin. The experimental results of EXAMPLEs 5-7 show that instead of application of a mixed composition, separate preparation and application of the anhydrous composition of small-molecule HA and the anhydrous composition of barrier HA lead to a superior skin moisturizing effect that general hydrous HA products could not achieve.

According to the aforementioned examples, compared with the hydrous small-molecule HA sample, the anhydrous composition of small-molecule HA of the present invention possesses the ability to penetrate across the horny layer of skin and increase kin hydration level. Moreover, application of the combination of the anhydrous composition of small-molecule HA and the anhydrous composition of barrier HA further improves skin hydration level and skin elasticity.

In conclusion, the formulation of the anhydrous composition of small-molecule polysaccharides provided in the present invention allows the small-molecule polysaccharide to maintain a molecular size of 12-22 nm, precluding an increased molecular size of over 40-50 nm, the size of the gap between keratinocytes in the horny layer of skin, caused by absorption of water from the composition and enlargement of the small-molecule polysaccharides. As a result, the small-molecule polysaccharide can penetrate directly across the horny layer of skin and effectively retain water in the epidermis of skin. The anhydrous composition of small-molecule polysaccharides provided in the present invention not only promotes the ability of skin to retain water, but also maintains skin hydration level for long time, leading to effective prevention of or improvement in wrinkle formation, skin laxity, or sunken skin.

What is claimed is:

1. A method of effectively maintaining skin hydration level in a subject in need thereof, comprising first administering to the subject an anhydrous composition of small-molecule hyaluronic acid and thereafter administering an anhydrous composition of barrier hyaluronic acid, wherein the anhydrous composition of small-molecule hyaluronic acid consists of a polyol and 2% w/v of a small-molecule hyaluronic acid having a molecular size of 12-22 nm, and the anhydrous composition of barrier hyaluronic acid consists of the polyol and 1% w/v of a barrier hyaluronic acid having a molecular weight of 1 MDa or more, and wherein the polyol is propylene glycol, glycerol, or combination thereof.

2. The method of claim 1, wherein the small-molecule hyaluronic acid has a molecular weight ranging from 4 kDa to 8 kDa.

3. The method of claim 1, wherein the small-molecule hyaluronic acid is obtained by hydrolysis of a hyaluronic acid by a hyaluronidase.

4. The method of claim 1, wherein the polyol is glycerol.

* * * * *